United States Patent [19]

Claremon

[11] Patent Number: 4,743,694

[45] Date of Patent: May 10, 1988

[54] DIASTEREOCONTROLLED SYNTHESIS OF 2-AMINO ALCOHOLS

[75] Inventor: David A. Claremon, Audubon, Pa.

[73] Assignee: Mercek & Co., Inc., Rahway, N.J.

[21] Appl. No.: 851,073

[22] Filed: Apr. 11, 1986

[51] Int. Cl.$^4$ ............... C07D 327/00; C07D 333/36; C07C 109/12; C07C 109/16
[52] U.S. Cl. ..................................... 549/4; 549/60; 549/68; 549/78; 549/214; 549/472; 549/480; 556/423; 564/250; 564/251
[58] Field of Search ............... 549/480, 68, 4, 60, 549/78, 80, 214, 472, 505; 564/250, 251; 556/423, 223

[56] References Cited

U.S. PATENT DOCUMENTS

| | | | |
|---|---|---|---|
| 3,882,124 | 5/1975 | Kirchlechner et al. | 260/351.3 |
| 3,897,453 | 7/1975 | Gante et al. | 549/43 |
| 3,943,132 | 3/1976 | Schirmann et al. | 564/251 |
| 3,948,949 | 4/1976 | Gante et al. | 549/388 |
| 4,644,011 | 2/1987 | Ballenegger et al. | 549/399 |

OTHER PUBLICATIONS

J. Org. Chem, 50 3752–3757 (1985), Roush, W. R.
J. Am. Chem. Soc., 107, 1797–8 (1985), Hirama et al.
J. Am. Chem. Soc., 106, 4629–30 (1984), Fugita et al.
Chem. Pharm. Bull, 20, 539–42, Yamada, S.
J. Am. Chem. Soc., 106, 7861–67, Garigipati et al.
Tetrahedron Letters, 26, 1261–64 (1985), Hanessian, S. et al.
Chem. Lett., 671–4 (1985), Majaiyama et al.
J. Org. Chem., 48, 909–10 (1983), Fuganti et al.
Helv. Chim Acta, 47, 1101–13 (1964), Marxer et al.
J. Chem. Soc., Chem. Commun., 668–9 (1979), Takahashi et al.

Primary Examiner—Richard L. Raymond
Assistant Examiner—Raymond Covington
Attorney, Agent, or Firm—William H. Nicholson; Michael C. Sudol; Mario A. Monaco

[57] ABSTRACT

The addition of organolithium to dimethylhydrazones of certain ethers of a-hydroxyaldehydes results in the synthesis of threo- or erythro- intermediates readily convertible to threo- or erythro-2-amino alcohols.

8 Claims, No Drawings

DIASTEREOCONTROLLED SYNTHESIS OF 2-AMINO ALCOHOLS

SUMMARY OF THE INVENTION

This invention is concerned with the diastereoselective synthesis of 2-amino alcohols such as norpseudoephedrine. The key step of the process is the diastereoselective addition of an organolithium reagent across the double-bond of an aldehyde dialkylhydrazone, the starting material having in place an ether of an a-hydroxy group thereof. The ether and the resulting hydrazine are hydrogenolyzed to the corresponding hydroxy and amino group respectively by standard procedures.

BACKGROUND OF THE INVENTION

Various stereoselective strategies have been devised for the synthesis of 2-amino alcohols, relying on: intramolecular opening of epoxides (Roush et al., *J. Org. Chem.*, 50, 3752 (1985)); intramolecular Michael reactions (Hirama et al., *J. Amer. Chem. Soc.*, 107, 1797 (1985); reduction of a-aminoketones (Fujita et al., *J. Amer. Chem. Soc.*, 106, 4629 (1984)); allylic sulfoxide 2,3-sigmatropic rearrangements of Diels-Alder adducts (Garig et al., *J. Amer. Chem. Soc.*, 106, 7861 (1984)); nitro-aldol reactions (Hanessian et al., *Tetrahedron Letters*, 26, 1261 (1985)); organometallic additions to a-alkoxyimines (Mukaiyama et al., *Chem. Lett.*, 671 (1985)); or organometallic additions to sulfinimines (Fuganiti et al., *J. Org. Chem.*, 48, 910 (1983) and Fronza et al., *J. Carbohydrate Chem.*, 2, 1225 (1983)).

The last strategies discussed above, i.e. organometallic additions, although attractive, are not entirely satisfactory inasmuch as isolation of imines is often problematic, and preparation of sulfinimines requires strongly basic conditions which may epimerize substrates.

Hydrazone derivatives of aldehydes and ketones have been used extensively as substrates for enolate derived chemistry affording chiral alkylation products quite resistant to racemization. However, only limited or preliminary reports of their electrophilic reactions with organometallic reagents have appeared (Takohashi et al., *J. Chem. Soc, Chem. Comm.*, 668 (1979) and Marxer et al., *Helv. Chim. Acta*, 47, 1101 (1964).

Surprisingly, we have found that 1,1-dimethylhydrazones provide high threo diastereoselectivity on reaction with organo lithium reagents and eliminate the problems associated with imine derivatives. The approach provides an attractive route to threo 2-amino alcohols after hydrogenolytic cleavage of the intermediate hydrazines.

DETAILED DESCRIPTION OF THE INVENTION

The key step of the novel process of this invention comprises the diastereoselective electrophilic addition of an organo lithium reagent to an a-alkoxy-aldehyde dialkylhydrazone, which can be illustrated by reaction Scheme I:

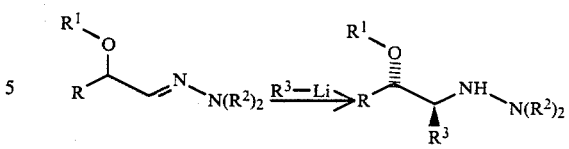

wherein:
R is
  (1) $C_{1-8}$ lower alkyl, either unsubstituted or substituted with phenyl or naphthyl which in turn can be substituted with:
    (a) $C_{1-3}$alkyl,
    (b) hydroxy-$C_{1-3}$alkyl, or
    (c) $C_{1-3}$alkoxy-$C_{1-3}$alkyl;
  (2) phenyl, either unsubstituted or substituted with:
    (a) $C_{1-3}$alkyl,
    (b) hydroxy-$C_{1-3}$alkyl, or
    (c) $C_{1-3}$alkoxy;
$R^1$ is
  (1) $C_{1-5}$alkyl,
  (2) phenyl-$C_{1-3}$alkyl,
  (3) $C_{1-3}$alkoxy-$C_{1-3}$alkyl,
  (4) benzyloxy-$C_{1-3}$alkyl,
  (5) trityl,
  (6) Si(phenyl)$_3$,
  (7)

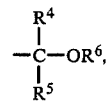

wherein $R^4$ and $R^5$ are independently $C_{1-5}$alkyl, and $R^6$ is $C_{1-5}$alkyl, or phenyl-$C_{1-3}$alkyl;
$R^2$ is $C_{1-3}$alkyl or phenyl; and
$R^3$ is
  (1) $C_{1-6}$alkyl, either unsubstituted or substituted with $C_{1-3}$alkoxy, $C_{1-3}$alkylthio, or tri($C_{1-4}$alkyl)-silyl,
  (2) $C_{1-6}$alkenyl, either unsubstituted or substituted with $C_{1-3}$alkoxy, $C_{1-3}$alkylthio or tri($C_{1-4}$alkyl)silyl,
  (3) phenyl,
  (4) furyl, or
  (5) thienyl.

In a preferred embodiment R is $C_{1-8}$alkyl (especially n-pentyl) or phenyl and $R^2$ and $R^3$ are both methyl.

If the desired amino-alcohol has an erythro-configuration then $R^1$ is trityl or —Si(Phenyl)$_3$ preferably trityl. If the desired amino-alcohol has a threo-configuration then $R^1$ is one of the other definitions provided above, and preferably benzyl, benzyloxymethyl or 2-methoxy-2-propyl.

The key step of this novel process is conducted in an anhydrous ethereal solvent such as diethyl ether, tetrahydrofuran (THF), 1,2-dimethoxyethane or the like, at low temperatures such as about $-20°$ to $0°$ C., preferably about $-10°$ C. in an inert atmosphere such as argon or nitrogen during the dropwise addition of the hydrazone to a slight excess of the organolithium reagent. The reaction is completed by removal of the cooling bath to permit spontaneous warming to ambient temperature (20°–25° C.) and holding it at that temperature about 0.5 to 2 hours.

After quenching the excess organolithium reagent by addition of sufficient water the reaction is worked up by standard purification procedures. It is convenient to acidify the mixture to about pH 2 with a mineral acid, preferably hydrochloric acid, wash with ether, separate the aqueous phase and basify to about pH 12 with caustic, such as aqueous sodium hydroxide, extract with ethyl acetate, wash the extract with brine, dry and concentrate to dryness. The resulting hydrazine is sufficiently pure to proceed with conversion to the 2-amino alcohol.

If in the above aqueous work-up the hydroxyl function were protected with an acid labile group, such as methoxy-2-propyl, the hydrazino alcohol is obtained directly.

This conversion to the amino alcohol is conveniently performed by catalytic hydrogenolysis with platinum oxide in a lower alkanol, especially methanol with about 1% by volume of acetic acid, at about $3.4 \times 10^5$ to $4.1 \times 10^5$ $Nm^{-2}$ (50 to 60 psig) of hydrogen at room temperature. The reduction is usually complete in about 3-4 hours.

If in the above hydrogenolysis the hydroxyl function had been protected by a hydrogenolytically cleavable protecting group such as a benzyl or benzyloxymethyl group then the free alcohol is obtained.

Other alcohol protecting groups generally known in the art as being inert to organolithium reagents are suitable for this process such as those described in "Protective Groups in Organic Synthesis" by T. W. Greene, (J. Wiley & Sons, N.Y., 1981) pages 10-87.

Some of the 2-amino alcohols preparable by the novel process of this invention are known compounds, such as norpseudoephedrine which is known to be useful as an anorexic agent and a chemical reagent in the optical resolution of externally compensated acids.

EXAMPLE 1

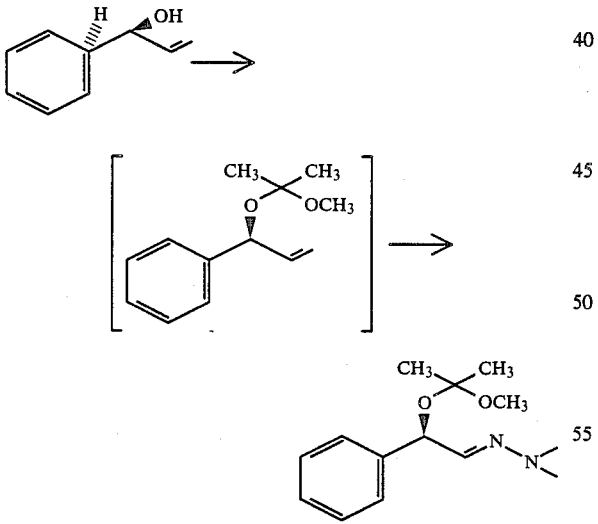

Step A:

To 498 mgs (3.71 mmols) of (S)-1-phenylallyl alcohol there was added with stirring 5 ml of 2-methoxypropene at $-10°$ C. under Argon and 1.0 mliter of POCl$_3$ was added. The cooling bath was removed and after 30 minutes at 25° C. powdered anhydrous K$_2$CO$_3$ (2 g) was added and stirring was continued for ½ hour. The reaction was diluted with ether, filtered through 5-10 m scintered glass funnel and concentrated on a rotary evaporator at reduced pressure. The crude oil was dissolved in 50 ml of CH$_2$Cl$_2$ and cooled to $-78°$ C. under argon. Ozone gas was introduced until a constant blue color appeared. The excess ozone was removed by an argon gas purge, and 2.0 ml of CH$_3$SCH$_3$ was added and the cooling bath warmed to $-35°$ C. 1,1-Dimethylhydrazine (2.0 ml) was added and the cooling bath warmed to $-10°$ C. over 1 hour. Anhydrous Na$_2$SO$_4$ (15 grams) was added and the reaction was warmed to 25° C. The mixture was diluted with 150 ml of CH$_2$Cl$_2$ and washed with H$_2$O ($3 \times 50$ ml) and 50 ml of saturated aqueous NaHCO$_3$:saturated aqueous NaCl (1:1). The organic phase was dried (Na$_2$SO$_4$), filtered and concentrated to an oil, yield 595 mgs which was immediately used without purification in the next reaction.

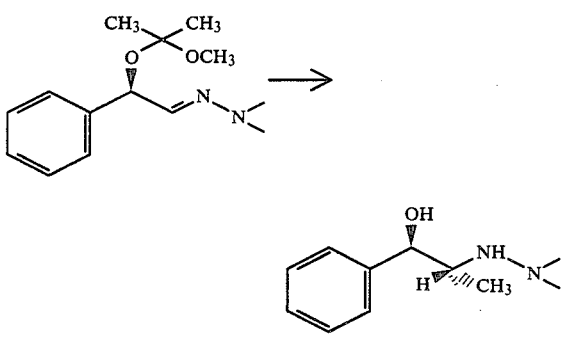

Step B:

The crude hydrazone (590 mgs, 2.38 mm) from Step A in 6 ml of anhydrous ether cooled to $-10°$ C. under Ar was treated dropwise in MeLi (2.5 ml of 1.4M solution in ether). After addition was complete, the cooling bath was removed and the mixture stirred for 1 hour at 25° C. The reaction was quenched by addition of H$_2$O (3 ml) and then acidified to pH 2.0 with 1.2M HCl in H$_2$O. The aqueous layer was washed with ether ($3 \times 30$ ml) and then basified to pH 12 with 40% NaOH in H$_2$O. The aqueous layer was extracted with ethyl acetate ($4 \times 50$ ml). The combined ethylacetate extracts were washed with saturated aqueous NaCl, dried (Na$_2$SO$_4$), filtered and concentrated to 408 mgs (89%) of an orange oil. The 300 mHZ 'HNMR contained only one major compound.

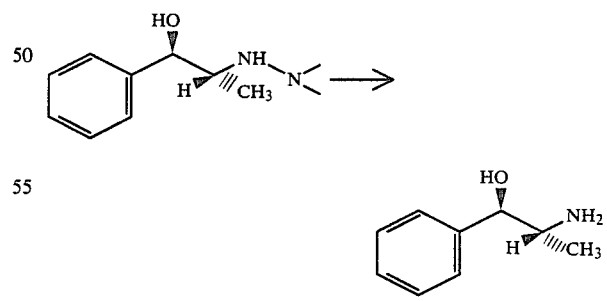

Step C:

158 mgs of the hydrazine in 16 ml of 1% acetic acid in CH$_3$OH was treated with 160 mgs of PtO$_2$ and shaken on a Parr apparatus at $3.4 \times 10^5$ to $4.1 \times 10^5$ $Nm^{-2}$ (50-60 psig) of H$_2$ for 3.5 hours. The crude product was obtained by filtration of the reaction mixture through filter aid and concentration on a rotary evaporator at reduced pressure. This residue was redissolved in H$_2$O (10 ml) and basified to pH 12.0 with saturated aqueous Na₂CO₃. Extraction with CH₂Cl₂ (3×35 ml), drying of the CH₂Cl₂ extracts (Na₂SO₄), filtration, and concentration at reduced pressure provided an oil which solidified on standing to give 113 mgs (92%) of a waxy white solid and this was dissolved in 2 ml of ethanol and cooled to 0° C. Ethanolic HCl was added until acidic (PH 4.0), then ether was added to precipitate the salt. The ¹HNMR, TLC and rotation were in agreement with commercially available (−)-norpseudoephedrine hydrochloride.

Similarly, (±)-1-phenylallyl alcohol is converted to (±) norpseudoephedrine by an identical procedure.

The diastereoselectivity of the reaction is demonstrated by the threo/erythro ratios shown in Table I of the products obtained by employing the procedures substantially as described in Example 1, Step B, but using the hydrazones and organolithium compounds also described in Table I.

TABLE I

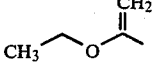

| $R^1$ | $R^3$ | % YIELD | RATIO THREO/ERYTHRO |
|---|---|---|---|
| PhCH₂OCH₂— | CH₃— | 95 | 97/3 |
| PhCH₂OCH₂— | Ph— | 95 | >98/2 |
| PhCH₂— | CH₃— | 98 | 97/3 |
| PhCH₂— | Ph— | 93 | >98/2 |
| PhCH₂— | CH₃OCH=CH₂ (vinyl ether) | 94 | >98/2 |
| PhCH₂— | (CH₃)₃C— | 98 | >98/2 |
| CH₃OC(CH₃)₂—⁽¹⁾ | Ph— | 93 | >98/2 |
| CH₃OC(CH₃)₂—⁽¹⁾ | furyl | 85 | >98/2 |
| CH₃OC(CH₃)₂—⁽¹⁾ | CH₃-Si(CH₃)₂-CH₂CH(CH₃)... | 88 | >98/2 |
| (Ph)₃C— | CH₃— | 85 | 1/10 |

⁽¹⁾Protecting group in starting material which is removed during aqueous work-up so that in the hydrazine product R¹ = H.

What is claimed is:

1. A process for the preparation of threo-2-amino alcohols which comprises the diastereo-selective addition of an organolithium reagent of formula R³-Li to an aldehyde hydrazone of formula:

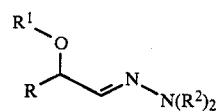

in an ethereal solvent at −20° to 0° C. in an inert atmosphere to produce the threo compound of formula:

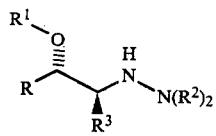

wherein:
R is
  (1) C₁₋₈ lower alkyl, either unsubstituted or substituted with phenyl or naphthyl which in turn can be substituted with:
    (a) C₁₋₃alkyl,
    (b) hydroxy-C₁₋₃alkyl, or
    (c) C₁₋₃alkoxy-C₁₋₃alkyl;
  (2) phenyl, either unsubstituted or substituted with:
    (a) C₁₋₃alkyl,
    (b) hydroxy-C₁₋₃alkyl, or
    (c) C₁₋₃alkoxy;
R¹ is
  (1) C₁₋₅alkyl,
  (2) phenyl-C₁₋₃alkyl,
  (3) C₁₋₃alkoxy-C₁₋₃alkyl,
  (4) benzyloxy-C₁₋₃alkyl,
  (5)

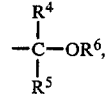

wherein R⁴ and R⁵ are independently C₁₋₅alkyl, and R⁶ is C₁₋₅alkyl, or phenyl-C₁₋₃alkyl;
R² is C₁₋₃alkyl or phenyl; and
R³ is
  (1) C₁₋₆alkyl, either unsubstituted or substituted with C₁₋₃alkoxy, C₁₋₃alkylthio, or tri(C₁₋₄alkyl)-silyl,
  (2) C₁₋₆alkenyl, either unsubstituted or substituted with C₁₋₃alkoxy, C₁₋₃alkylthio or tri(C₁₋₄alkyl)silyl,
  (3) phenyl,
  (4) furyl, or
  (5) thienyl;
followed by catalytic hydrogenolysis of the R¹- and the —N(R²)₂ group.

2. The process of claim 1 comprising the step of addition of R³-Li to an aldehyde hydrazone of structure:

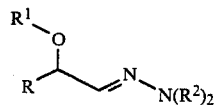

3. The process of claim 2 wherein R¹ is hydrogen, benzyloxy or benzyloxymethyl; R is C₁₋₈alkyl or phenyl, and R² and R³ are both methyl.

4. The process of claim 3 wherein R is phenyl.

5. A process for the preparation of erythro-2-amino alcohols which comprises the diastereoselective addition of an organolithium reagent of formula $R^3$-Li to an aldehyde hydrazone of formula:

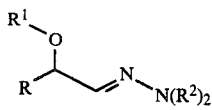

in an ethereal solvent at $-20°$ to $0°$ C. in an inert atmosphere to produce the erythro compound of formula:

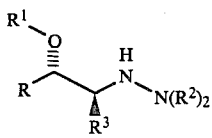

wherein:

R is
  (1) $C_{1-8}$ lower alkyl, either unsubstituted or substituted with phenyl or naphthyl which in turn can be substituted with:
    (a) $C_{1-3}$alkyl,
    (b) hydroxy-$C_{1-3}$alkyl, or
    (c) $C_{1-3}$alkoxy-$C_{1-3}$alkyl;
  (2) phenyl, either unsubstituted or substituted with:
    (a) $C_{1-3}$alkyl,
    (b) hydroxy-$C_{1-3}$alkyl, or
    (c) $C_{1-3}$alkoxy;

$R^1$ is
  (1) trityl,
  (2) Si(phenyl)$_3$;

$R^2$ is $C_{1-3}$alkyl or phenyl; and $R^3$ is
  (1) $C_{1-6}$alkyl, either unsubstituted or substituted with $C_{1-3}$alkoxy, $C_{1-3}$alkylthio, or tri($C_{1-4}$alkyl)silyl,
  (2) $C_{1-6}$alkenyl, either unsubstituted or substituted with $C_{1-3}$alkoxy, $C_{1-3}$alkylthio or tri($C_{1-4}$alkyl)silyl,
  (3) phenyl,
  (4) furyl, or
  (5) thienyl;

followed by catalytic hydrogenolysis of the $R^1$- and the $-N(R^2)_2$ group.

6. The process of claim 5 comprising the step of addition of $R^3$-Li to an aldehyde hydrazone of structure:

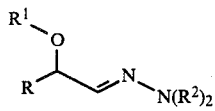

7. The process of claim 6 wherein $R^1$ is trityl; R is $C_{1-8}$alkyl or phenyl, and $R^2$ and $R^3$ are both methyl.

8. The process of claim 7 wherein R is phenyl.

* * * * *